United States Patent [19]

Joseph et al.

[11] Patent Number: 5,410,297
[45] Date of Patent: Apr. 25, 1995

[54] CAPACITIVE PATIENT PRESENCE MONITOR

[75] Inventors: Peter Joseph, Bayside; Peter Scharpf, Hartford; Eric T. Heinze, New Berlin, all of Wis.

[73] Assignee: R. F. Technologies, Inc., Milwaukee, Wis.

[21] Appl. No.: 2,929

[22] Filed: Jan. 11, 1993

[51] Int. Cl.$^6$ ............................................. G08B 21/00
[52] U.S. Cl. ..................................... 340/573; 340/666
[58] Field of Search ............................ 340/573, 666

[56] References Cited

U.S. PATENT DOCUMENTS

| | | | |
|---|---|---|---|
| 3,760,794 | 9/1973 | Basham | 340/573 |
| 3,925,762 | 12/1975 | Heitlinger et al. | 340/573 |
| 4,051,522 | 9/1977 | Healy et al. | 358/86 |
| 4,179,692 | 12/1979 | Vance | 340/573 |
| 4,295,133 | 10/1981 | Vance | 340/573 |
| 4,484,043 | 11/1984 | Musick et al. | 200/85 |
| 4,700,180 | 10/1987 | Vance | 340/573 |
| 4,907,845 | 3/1990 | Wood | 340/573 |
| 5,144,284 | 9/1992 | Hammett | 340/573 |

*Primary Examiner*—Glen Swann

[57] ABSTRACT

A capacitive sensor pad includes a foam plastic pad and heavy aluminum foil plates located to the opposite side thereof. The plates are adhesively bonded to the inner surfaces of an outer cover. The capacitor of the pad is connected in circuit with an oscillator and produces a frequency-related output. A ripple counter establishes a frequency-related output proportional to the capacitance. A microprocessor reads the counter output and a plurality of samples are averaged to establish a reference base and the true weight affect of the patient on the sensing pad. Other factors which might effect the signal are readily attended to by programmed compensation. Each subsequent sample is averaged and compared with the reference base. If within a permitted range, the latest and current signal is averaged with the reference base and establishes a new base, and continuously tracks changes in the sensing system. A selected change in a selected time delay system by requiring a series of alarm states or immediately if advance warning is desired, actuates an alert or alarm system, which requires positive resetting to terminate the alarm system. The system is positively reset to return to normal position monitoring. The system may be set to automatically reset the alarm system after an alarm condition is established and then removed by the continuous tracking of the patient movement.

17 Claims, 3 Drawing Sheets

CAPACITIVE PATIENT PRESENCE MONITOR

BACKGROUND OF THE INVENTION

This invention relates to a monitoring apparatus to monitor the presence of a patient in a supporting structure such as a bed, a chair or like supporting device.

Patients or residents are often restricted to a bed, chair, or other supporting structure for various reasons, primarily related to their well being and safety. Monitoring is significantly important in a restricted free environment for protecting the dignity of people. Additionally, a patient may at times refuse conforming to restrictive requirements, or may accidently or inadvertently attempt to move themselves because they forget the ability to make a rational decision is impaired or the like which may prevent following instructions. If a patient inadvertently or accidentally leaves or attempts to leave a support and immediately returns, it may not be necessary to indicate such a minor occurrence. If they move from the support for any period of time or start to leave, which for some individuals may be on the order of seconds, an alarm may be necessary. This aspect of monitoring would require different response characteristics of the monitoring system. Thus, it may be desirable to minimize and avoid unnecessary reaction to non-adverse movements of one patient, while others may require immediate attention to unauthorized movement. This invention thus also may provide advance notice of a patient or resident leaving a chair or bed before they actually do so.

Further, the monitoring systems are used in rather widely and different environments including atmospheric conditions, and sensor quality may deteriorate with age, changes in the weight of the patient and other similar variables which are widely encountered in the health care field. A most satisfactory system should operate in the various settings and requirements.

Prior art systems have generally used on/off sensing unit for actuating an output alarm unit. For example, U.S. Pat. No. 4,179,692 which issued Dec. 18, 1979 and the related U.S. Pat. No. 4,295,133 which issued Oct. 13, 1981, disclose systems in which on/off switch generates binary signals in response to the movements of the patient to and from the bed. A time may be used to delay an alarm, which also prevents effective advance warning. The latter patent provides a switch which is sensitive to movement within the bed to generate on/off signals reflective of movement within the bed structure. Thus, if a patient is sufficiently restless, movement of the patient creates closure of the switch more often than is considered normal. Charging and discharging of a capacitor is controlled by on and off status of the switch and provides a threshold signal under conditions which are considered sufficiently adverse to trigger an alarm. Various switch systems are illustrated including spring loaded switch units which respond to patient movement, or support members which hold contacts in spaced relation with the contact being deformed by the patient movement to thereby change the switch between on and off status. In all instances, a distinct step movement is required and a pressure sensitive device provides a digital on/off output signal.

A similar system is shown in the more recently issued U.S. Pat. No. 4,700,180 which also discloses a binary signal generating sensor. This system responds whereby a patient lying down on a bed establishes a first switch position. When the patient moves from the bed or even moves to the edge of the bed, the switch changes to its alternate state thereby providing a binary signal similar to that of the other prior art references. The on/off signal, again, is a step function signal in a processing system to respond and provide an appropriate alarm. The '180 patent also discloses a sandwich-type construction with a thin compressible insulating material having a central opening. Contacts are secured to the opposite faces of the insulating mat spanning the opening. The patient lying on the mat compresses the insulating mat and moves the conducting wires into a closed circuit condition. A somewhat similar device is shown in a prior art patent U.S. Pat. No. 4,484,043 which issued Nov. 20, 1984. U.S. Pat. No. 5,144,284 which issued September, 1992 discloses a pressure sensor having foil elements separated by a foam element. With a low voltage applied to the plates, a change in electrical resistance or capacitance is created and detected by the device.

In nursing homes, retirement homes, hospitals and like facilities, various degrees of activities are permitted for different patients. It becomes extremely difficult with present day technology to provide for the necessary monitoring of these various patients with such widely varying characteristics with present day switching systems.

The inventors' analysis and investigation has resulted in a unique realization of the sources of the problem associated with present day devices available for patient monitoring with respect to a given support structure. Generally, the inventors realized that the sensing switches only provides a binary signal generating devices which has limited the response system. In particular, the processing of the on/off switch signals limits the ability to continuously track the movement of the patient. This basic approach, which appears to be uniformly used in the prior art known to the inventors, finds severe limitation on the ability of the system to respond to the varying patient characteristics, and significantly the operating environment within which the patients live and the systems operate.

SUMMARY OF THE PRESENT INVENTION

The present invention is based on providing of a complete continuous tracking system which not only provides a continuous tracking of the patient movement but permits operation in different environmental conditions and control characteristic for different patients with varying weights, heights and shapes. Generally, in accordance with the present invention, a sensing unit is secured to the support structure and is responsive to patient movement on and within the structure as well as from and to the structure, with the output characteristic of the signal providing continuous information with respect thereto. In addition, various other inputs may be coupled into the processing circuit to permit the appropriate response of the processed signal. The system may operate in different atmospheric conditions such as humidity, temperature and the like.

The system also provides and permits processing with unique response characteristics, such as an automatic reset of the system to an initial state in response to a momentary alarm-type movement of the patient. In addition, the characteristic of the sensing unit senses low patients weight and as a result of its physical properties is generally not adversely affected by accumulated dirt, moisture, or other foreign matter and does not prevent reliable operation of the system.

More particularly, in accordance with a first unique feature of the present invention, the sensing unit is a capacitive sensor member preferably in the form of a substantially flat pad which is placed beneath the patient. The pad has a weight responsive capacitance characteristic which varies continuously with the patient's weight and movement. In a practical application and a preferred embodiment, the sensing unit consists of an inner relatively thin resilient electrically insulating member, such as a foam plastic. Capacitive plates of a compliant construction are located to the opposite sides of the insulating and dielectric material to form a capacitive sensing unit. An outer protective cover encloses the unit. Signal terminals are connected to the respective capacitive plates and coupled as basic signal input to a processing circuit, and particularly to a programmable signal processing circuit such as a microprocessor for optimum system response and patient control. The use of a processor compensates for the use or application of a pad, permitting the pad to be used in different supports.

In a preferred construction, each capacitive plate is formed of a compliant thin material such as a heavy aluminum foil. The foil is laminated or otherwise intimately secured to the opposed inner surfaces of the outer cover and is located in effective abutting relation with the resilient insulating member. The pad structure is secured to the support structure preferably in slightly spaced relation to the patient, and preferably located upon the top of the mattress.

For sensing the capacitance in an optimum system, the capacitor of the sensing unit cable is connected in circuit with a high frequency current source and the output is coupled to a counter to establish a pulsed output directly related to the capacitance. Samples are read in minute periods on the order of microseconds, and a plurality of samples are averaged or otherwise processed to establish a reference base. The signal generated in each sample varies directly with the capacitance and the true weight effect of the patient on the sensing pad. Other factors which might effect the signal are readily attended to by programmed compensation within the signal processing system. Thus, each sample is averaged and compared with the base reference signal, which is an average of a plurality of immediately prior existing samples. If within a selected range, the latest and current signal is averaged with the base reference signal to establish a new base level. The system thus continuously tracks the changes in the capacitance and the patient's weight. If a selected significant change is encountered within a selected time delay, an appropriate output is generated indicating the unwanted and apparently undesirable condition, and an alert is given by any suitable alarm device. The system requires positive resetting of the circuit to terminate the alarm.

The processing circuit with present day technology includes a microprocessor suitably programmed to respond to the output signal from the capacitance sensor and particularly the pulse count generated by the signal processing circuit. In a practical implementation, the capacitance sensor pad is coupled to an oscillator to generate a high frequency signal, the frequency which varies with the weight on the pad. A ripple counter couples the output signal to the microprocessor as a frequency width modulated signal proportioned to the weight. The processor has a very high frequency clock which generates a count within each cycle of the modulated signal. The count is averaged to produce a signal related to the weight. Initially, a number of samples are averaged to establish a base reference signal for the particular patient. The system then continues to take samples and each sample is similarly transmitted and its average is compared to the base reference signal, and the average level changed to track the weight change, if any. Generally, the processor preferably includes a circular buffer to continuously update the reference level.

If the average increases above a selected threshold, an alarm is established, preferably at the support location and at the remote station. With the high speed monitoring system, the system may be programmed to require a series of samples all within the alarm state before actually setting the alarm.

Once set, the alarm must be positively reset to return to normal position monitoring. A microprocessor permits programming of other characteristic inputs for simultaneous processing with the signal condition and thereby permit recognition of any other factors which may affect such signal other than that of the patient movement. Thus, the weight of the patient is automatically compensated for by the initial sampling to establish a reference base. The only limitation is the patient weight be sufficient to act on the capacitance sensor pad. By compensating such extraneous features and elements, the output signal provides a continuous tracking of the patient movement and thereby optimal monitoring of the patient placement on and within the support structure.

In accordance with a significant feature of the preferred embodiment, the system may be selectively set to automatically resets the alarm system after an alarm condition is established and then removed by the continuous tracking of the patient movement. The patient may therefore leave the bed or other support structure and return during the alarm period. The patient will generally return in reaction to setting of the alarm, and provides a reminder to the patient.

The control system is operated from a low voltage source, and particularly in a preferred construction from a high quality nine volt battery or other suitable power source. The condition of the battery is continuously monitored, and if the voltage level drops below a selected minimum acceptable level, a special alarm signal is generated, but the system continues to operate until the battery is completely discharged. In the practical installation, if the battery or other power source falls below a selected voltage, a unique related alarm is generated providing a clear indication to those in control of the power source.

The present invention provides a reliable position monitor which can operate with different weight patients and in varying environments. The system is readily constructed with present day technology at a cost effective level.

BRIEF DESCRIPTION OF THE DRAWINGS

The drawings provided herewith illustrate the best mode contemplated for carrying out the invention and are described hereinafter.

In the drawings.

DESCRIPTION OF THE ILLUSTRATED EMBODIMENT

Figure 1:
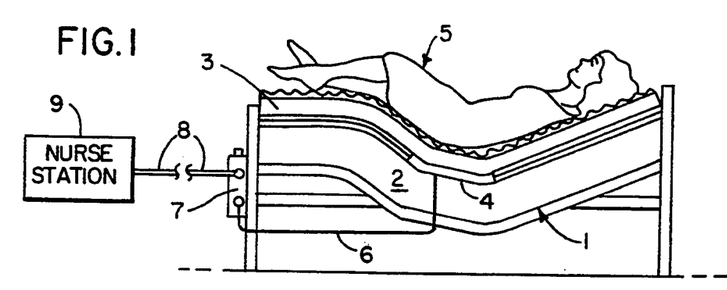
FIG. 1 is a pictorial view of a bed including a sensor unit.

Referring to the drawings and particularly to FIG. 1, a pictorial view of a bed unit with an alarm structure in accordance with this invention is disclosed. Bed 1 includes a typical mattress 2 with a top mattress pad or decubitus pad 3 thereon. The description refers to a bed for simplicity of explanation but may be any other structure. Existing uses in this art have included beds, chairs of all forms, inclined supports of residents and the like. Such uses are not however restrictive of the possible uses of the present invention.

A capacitance sensor unit 4 is located between the pad and the mattress. As more fully developed hereinafter, the sensor extends substantially across the width of the bed and is located under the pad in the crease of the bed. The sensor unit 4 establishes a varying capacitance signal which is connected via a cable 6 to a signal module 7 secured to the bed frame or the like. Signal module 7 includes the circuitry responsive to the output of the sensor unit and may include a local alarm as well as on/off controls, signal lights and the like. Generally, a cable 8 is connected from the module to a remote nurse station 9 when used in a hospital, nursing home or the like. In other applications of course, a cable may connect the output of the module or the signal from the module to any remote location.

The present invention is particularly directed to the construction of the capacitance responsive sensor unit 4 to provide a continuously varying signal related to the presence of a patient, not shown, within the bed, the patient's movement from the bed and movement within the bed, so as to monitor any unauthorized exiting therefrom. The circuit and controls responsive to such variation and capacitance is contained within the signal module 7, which provides a further aspect and feature of the present invention. The bed, mattress and other elements are well known. As a result, the sensor unit and signal module are presently described in detail with reference to the other elements only as necessary for a complete and full description of the illustrated embodiment of the invention.

Figures 2, 4, 7:
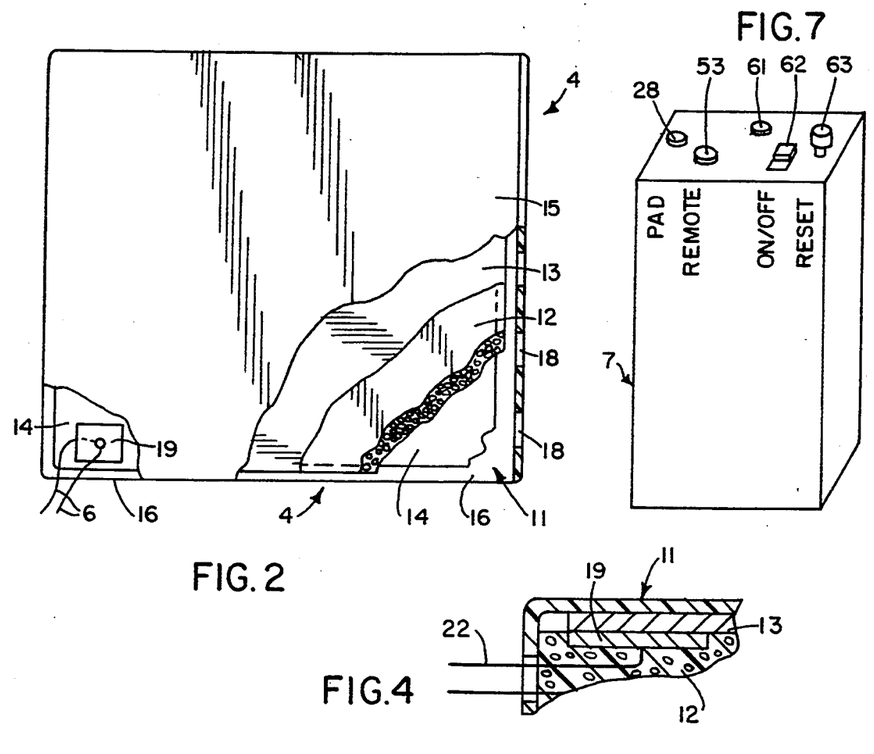
FIG. 2 is a plan view of the sensor unit.
FIG. 4 is a fragmentary enlarged cross-sectional view of the pad.
FIG. 7 is a pictorial view of the signal module.
Figure 3:
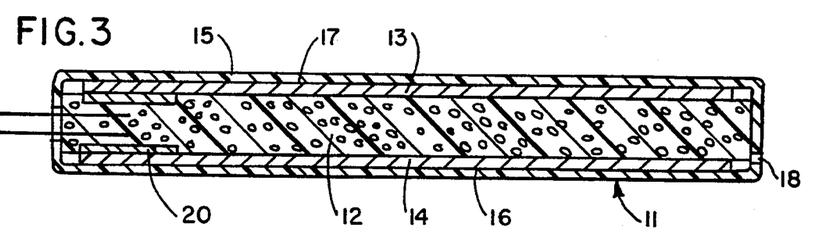
FIG. 3 is an enlarged cross-sectional view of the pad taken on line 3—3 of FIG. 2.

The capacitive sensor unit 4, as most clearly shown in FIGS. 2-4, includes a capacitor 10 enclosed within an outer cover 11. Cable 6 connects the capacitor to the module 7.

The sensor unit 4 is a generally rectangular thin pad of a width to substantially cover the width of the bed and a length to cover a portion of the bed within which the patient is located when in the bed in accordance with instructions.

The cover 11 is formed of a non-conductive material and typically of a suitable plastic for purposes of cleaning and the like. The cover 11 must be nonconductive to avoid interfering with functioning of the capacitor 10. The cover 11 is preferably formed of material which does not slip within the supporting location with special non-slip strips. The cover 11 may also be a breathable material to allow air flow through the sensor.

The capacitor 10 includes a central electrical insulating member 12 with slightly smaller capacitor plates 13 and 14 abutting the opposite faces of the insulating member 12. The member 12 is resilient and has a suitable dielectric constant, with the capacitance directly related to the spacing of the capacitor plates 13 and 14. The spacing of the plates automatically is accounted for in the controller so when connected it is directly proportional to the weight and location of the patient in the bed 1, and the capacitance sensor unit 4 thus provides a continuously varying capacitance related to the presence of the patient in the bed.

In a practical application, a 20"×30" sensor pad 4 was constructed. The sensor pad 4 includes an outer film cover 11, and a polyethylene which is white opaque in color has been used. Heavy duty compliant foil plates 13 and 14 such as an aluminum foil which is cost effective, copper which is more costly but is a better conductor are bonded to the inner surface of the top and bottom polyethylene film sheets 15 and 16 of the cover 11. A spray adhesive 17, such as 3M's number 77, provides for a proper bond. The use of a relatively heavy aluminum foil, such as readily found in domestic home use, has been found to provide satisfactory capacitor plates with a sufficient degree of conductivity. A printed ink may be used but special consideration must be given to establish a plate with proper conductivity. A one-quarter inch thick foam pad or layer 12 of polymeric foam such as a soft polyurethane is interposed between the foil plates 13 and 14. The material and the thickness of the pad is selected to produce a proper and effective capacitance with the weight of the patient, and comfort of the patient or resident without even knowing the pad is present. Prior sensor units generally are hard plate-like members which will be noticeable to the patient and may be uncomfortable. The outer sheets 15 and 16 of the cover are edge bonded to each other as at 17 to substantially enclose the capacitor defined by the bonded foil and the interposed foam layer. Small openings 18, such as edge slits, are formed in the periphery of the cover 11 to permit air interchange, and particularly to eliminate air entrapment. This permits a rapid and continuous response of the capacitance sensor to patient weight and movement. Thin copper elements 19 and 20, such as copper tape, are soldered one each to the heavy aluminum foil to establish connecting terminals. Each terminal may be one inch square. The cable includes separate lead wires 21 and 22 of the cable 6 are connected, generally to the center of the terminals, and the cable 6 extends outwardly through an appropriate opening in the overlapping sealed edges of the cover. The outer end of the cable 6 terminates in an input connector 23 for coupling to a signal modifying circuit in the module 7.

The sensor unit 4 being totally capacitive in response and relying on the enclosed sensing capacitor structure is essentially independent of the environmental conditions, such as temperature, humidity and the like. The large capacitor plates 13 and 14 provided by the extensive capacitive film attached to the structural cover 11 establishes a highly sensitive response to the movement of the patient relative to the support structure. Further, with the appropriate resiliency of the interposed insulating member 12 structure, the unit responds rapidly to changes in effective weight on the pad.

As presently developed, there is essentially no delay in the response of the system, except as specifically introduced, because the system responds to the change in the capacitance level and does not require a step movement or any physical interengagement of the sensing components, such as encountered in the step functions involved in typical switching systems of the standard sensing system in prior art installation which are commercially available and as generally disclosed in the prior art.

Figure 5:
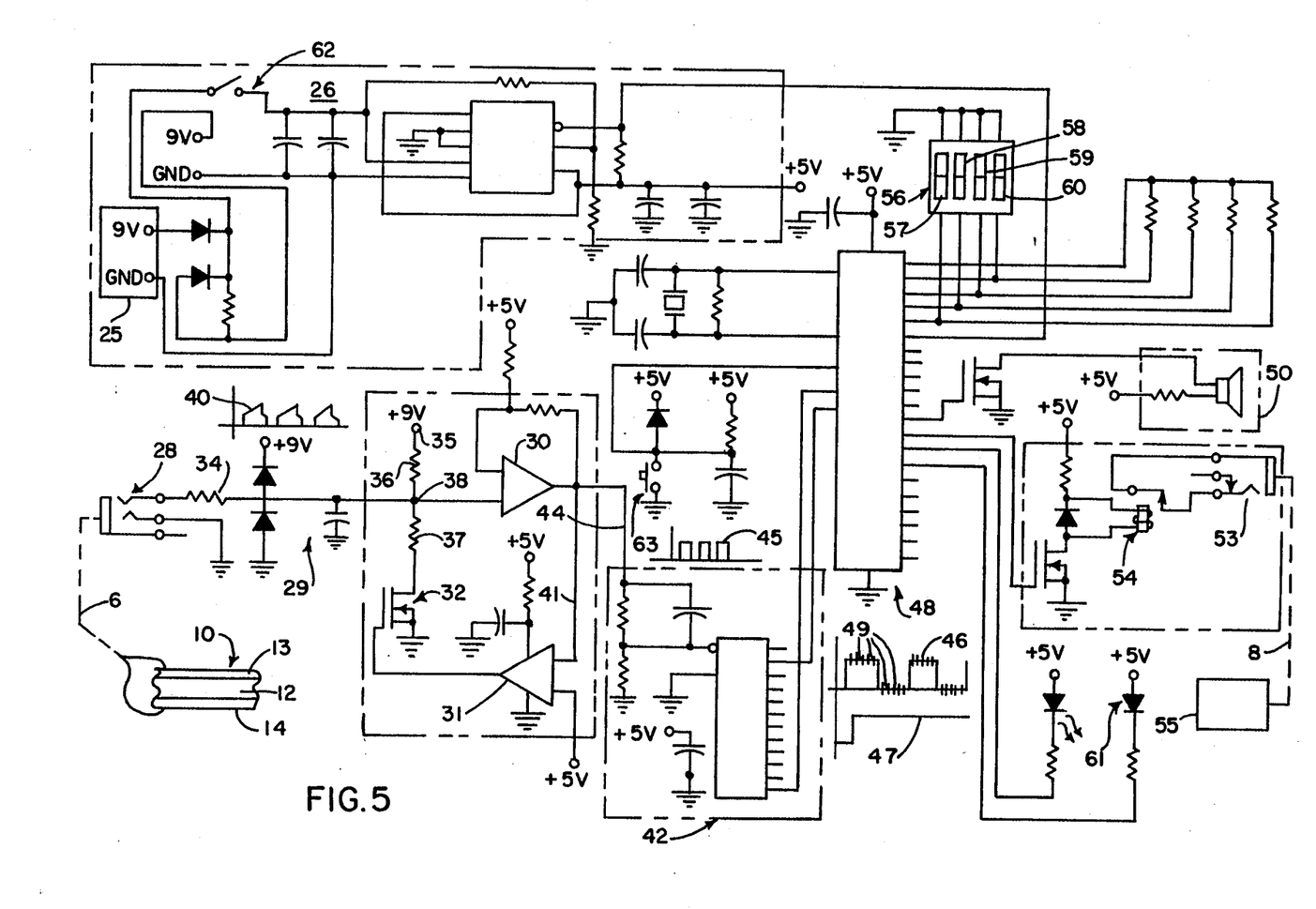
FIG. 5 is a schematic circuit diagram of the sensor capacitor, the interface circuit and the signal processing and alarm circuit of a preferred embodiment.

A typical bed alarm circuit is illustrated in FIG. 5. A nine volt battery 25 supplies power to a regulated supply circuit 26 for establishing necessary output voltages for operating of various components of the signal processing circuit. The circuit 26 is a typical known circuit and no further description is therefore given.

The processing circuit, as more fully developed hereinafter, is based on a pulse counting technique which responds to the frequency and pulse rate variation generated by a change of pad capacitance.

A frequency signal generator 27 is connected in circuit by a typical phone jack connector 28 with the capacitor plates and creates a high frequency current in the circuit including the capacitor, as shown at 29.

The capacitor plates are connected to the generator 27 using the pair of separate wires 21 and 22 to connect the capacitance signal of the sensor pad into the signal processing circuit. Using a two wire system, provides for an appropriate sending of the capacitance signal with the frequency and the voltage essentially corresponding to that anticipated based on the capacitor design of the sensor. Other forms of cable, such as a shielded wire may introduce additional capacitance into the circuit and vary the output waveform, unless otherwise compensated.

The generator 27 is shown as an oscillator including a pair of comparator amplifiers 30 and 31 and a switching transistor 32. The connection of the sensing capacitor by the cable into the circuit including a diode-capacitor network 33 and a series resistor 34. The switching transistor 32 is connected to the battery supply 35 via a voltage dividing network including resistor 36 and 37, with sensing capacitor network 33 connected to the common node 38 of resistor 36 and 37. The node is also connected to the negative input of comparator amplifier 30.

The oscillator includes the pair of comparator amplifiers 30 and 31 connected to control the transistor 32 and generate a high frequency signal in the sensor capacitor, such as shown at 40. The switching transistor 32 is a MOSFET transistor, which has been found to provide a stabilized switching of the circuit with the proper waveshape and frequency. The frequency of signal 40 is dependent upon the R-C time constant established by the sensing capacitor and the circuit resistors.

The high frequency signal from the oscillator amplifier 30 is fed back to amplifier 31 via line 41 and to a counter chip 42 via line 44, shown as a 4020 ripple counter. The signal is a square wave signal 45 having a frequency or repetition rate corresponding to the frequency of the signal 40. The counter 42 generates a square wave output signal 46 with a frequency proportional to the sensed capacitance related signal 40 and 45. The counter 42 is a divider and reduces the frequency of the pulses 46 and also generates an extended low frequency pulse signal 47 which is connected to activate a microprocessor 48 for processing of signal 46. The signal is a relatively low frequency signal, typically 333 Hz, which varies with the weight on the pad. The signal is compared to an internal clock of the processor, which clock operates at a significantly higher frequency such as 500 KHz.

Thus, each time period or pulse of the signal 46 is divided by the processor 48 and the number of cycles counted within the time of each pulse width, as shown at 49 on signal 46. Thus, a maximum of 500 times diversions or slices are possible. The actual number of time slices or counts varying with the weight applied to the sensor unit, and particularly the compression of the pad and the related capacitance. By comparing of changes in the count, the weight on the pad can be determined.

In a practical application, an initial sample cycle is read including a plurality of successive time periods, for example, four sequential samples, each covering approximately two seconds. The several samples in the cycle are completed in eight seconds, averaged, and stored in a suitable memory for comparison with the result of the subsequent sample periods and the level store in the memory.

A current sample is taken and compared with the base reference value created by the four samples. If the current average changes with respect to the last few averaged samples by a selected percentage, such is noted. Subsequent new samples are then compared with the base reference value to determine if the system has attained its previous average and a selected change level exist an alarm condition may be present. If so, an alarm triggers. If it does return to the previous average, the system will not alarm and the system returns to taking current samples which are compared to the base reference value, as described above.

The output of the processor 48 is connected to an audible alarm 50 mounted within the module via a switch transistor 51. A relay circuit 52 is connected via a switch transistor 52a to an output port of processor 48 for connection to the remote cable 8 via phone jack 53. The relay 54 of circuit 52 connects the remote alarm 55 into a suitable powered circuit for operating the remote alarm, which may be audible, verbal, visual, a combination thereof or any other suitable alert or alarm system.

In addition, the processor includes a series of selection control switches 56. The switches 56, in a practical system, includes a mute switch 57 which disable the output port to local alarm 50 while maintaining the remote alarm 55 active. A switch 58 permits adjusting the response characteristic to respond immediately to a signal level in excess of a threshold level, rather than allowing a series of successive alarm conditions to occur before triggering the alarm. A switch 59 allows adjustment of the threshold level to one of two different levels. A final switch 60 allows setting of the system to establish an automatic reset of the alarm system if, after an alarm, the patient returns to a proper position within the bed. An LED 61 is connected to output ports and driven on to identify the status of the systems, such as the turn-on of the system, an alarm state or the like. An on-off switch 62 controls supply of power to the system and a reset switch 63 provides for manual resetting of the alarm circuitry.

More particularly in a practical system, when first turned on, the processor reads and average a plurality of sensor samples, typically four samples. Each sample is taken in a short time period, typically in about two seconds requiring approximately eight or sixteen seconds for the base sampling and storing of the average in a buffer or the like. This automatically establishes a weighted base signal level for the particular patient. The circuit is then in a state to monitor changes in the capacitance of the sensor pad 4 and thereby the weight and/or movement of the patient. During each individual sample time period thereafter, the circuit reads a new or current sample, i.e. approximately every two seconds in this example. This new sample is compared to the base signal level in the buffer which is the average of the previous four samples. If the new sample signal is higher than the base signal level within a selected limit, the weight on the pad has decreased. This new sample is placed in the buffer and raises the average value of the reference signal in the buffer. The microprocessor 48 stores the signal in a circular buffer, not shown. In the counter, the additions of the new sample results in the removal of the first sample then in the buffer. Thus, the system continuously tracks any change including each decrease or increase in the effective weight on the pad on an instantaneous time period for all practical requirements.

However, if the new or current sample is lower than the base signal level of the previous four samples, this indicates that there is more weight. This sample is similarly compared to the base signal level, the current sample is averaged and placed into the buffer and lowers the average value of the base signal in the buffer.

The system will thus track any gradual increase or decrease in the weight on the pad.

If the decreasing change is in excess of the selected limit as set by the control switches 58 and 59, the sample is not added to the buffer because this is considered to be an alert or alarm condition. If switch 58 is closed, any level above the threshold level, triggers the alarm and the current signal is not added to the buffer. Similarly, if switch 58 is not closed, the system responds to the setting of switch 59 which sets the threshold as a percentage of the average. The current signal may or may not then create an alarm state. However, even though it is abnormal, the system again recycles and establishes a new current sample, compares that latest sample with the previous reference signal level without inclusion of the abnormal and alarm level signal. This last sequence continues until a selected number of alert conditions in a row are sensed. This is considered a true alarm condition, and an alarm is triggered. The number of successive sequenced conditions may be set between one and three in a practical program, as subsequently discussed. This total sequence takes approximately between two and six seconds. If less than selected number of alerts are created in a sequence or row, this is considered a minor shift in the position of the patient, the alert system is reset and the system operates and returns to normal operation with the next or current sample processed in accordance with the above described normal state in which such sample is added to and modifies the base reference signal.

The switch 60 provides an automatic alarm reset for optional patient monitoring. After an alert, the system continues to take samples, each of which is again compared to the existing alarm reference value, and if within the limits, modifies the reference value. If the patient thus returns to an acceptable position in the bed, the reference value will decrease indicating the alarm condition has been corrected. If the patient returns before service, the system turns off the alarm, and resets the system to again require a new series of alarm conditions to sound the alarm. For example, a patient may stand up, hear the alarm, sit down and thereby turn off the alarm. The patient, and the remote station, are however notified by the alarm and reset that an unacceptable movement and/or position from or within the bed has been made, and corrected. The patient will recognize this as a reminder of the specified violation of the restriction.

The samples are taken directly at the bed module with the battery powered module. The battery is continuously monitored and if the voltage thereof drops below 7½ volts, an alarm is set off which is unique; for example, a pulsed signal with a unique pulse rate. The system continues to operate however providing full monitoring of the patient's position and location in the bed until the battery is completely discharged. If the sensor is operatively disconnected from the module either by a malfunction of the sensor, failure to properly connect the cable or other defect, the system detects the failure and sounds the alarm.

A flow chart establishing the above programmed control of the system is shown in FIG. 7 and is briefly described based on the previous description.

Figure 6:
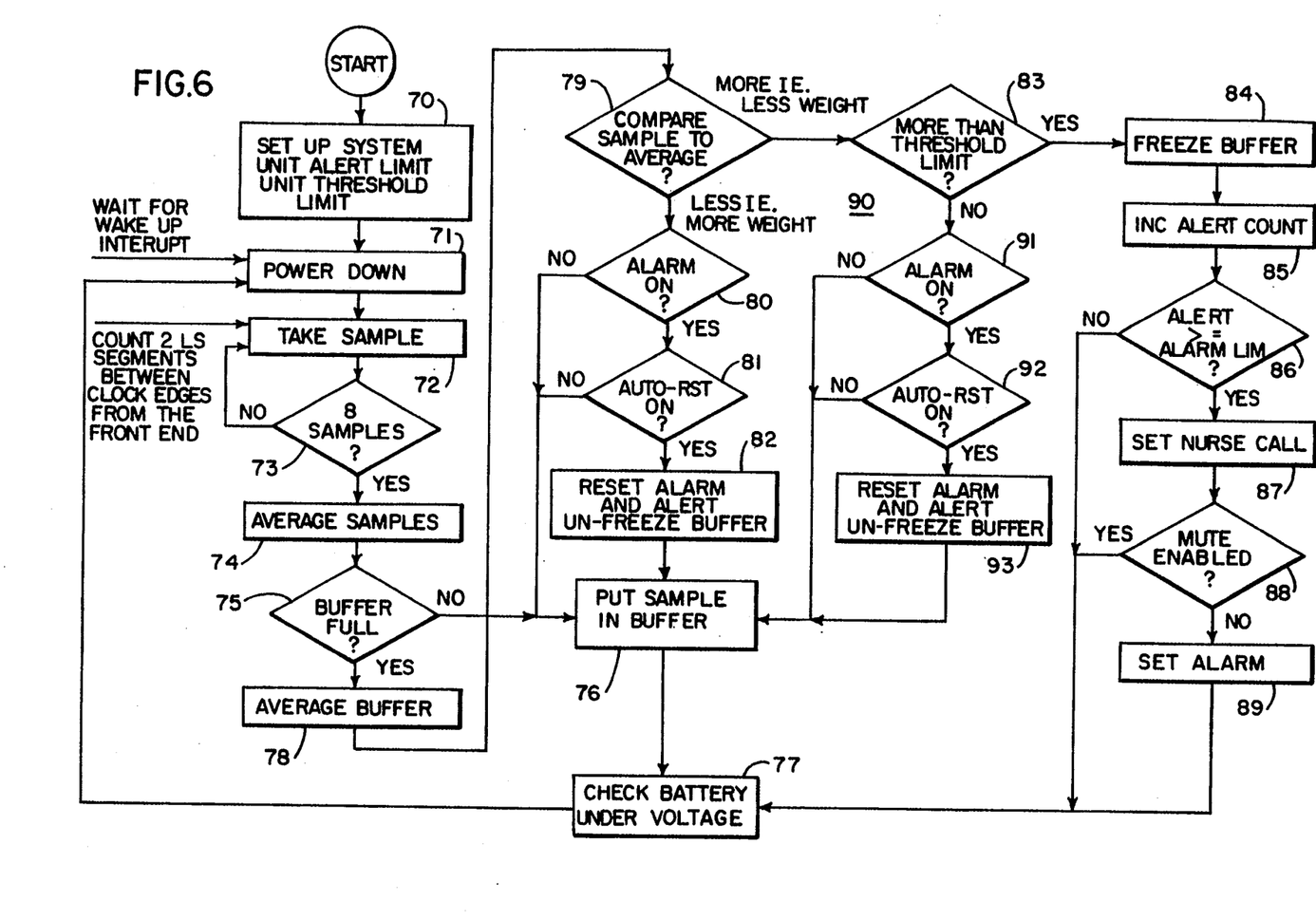
FIG. 6 is a flow chart of a processor program.

Referring to the program flow chart of FIG. 6, in the initial start-up of the system, and with reference to point 70, the user inserts the number of the alarm conditions that are to be created before an actual alarm is actuated by setting an alert counter shown in the flow chart, FIG. 6. Switch 58 of the selection switch 56 would set the alert counter for response to one alert condition. Switch 59 establishes a necessary differential between the reference signal and the new or current sample to establish an alert condition. Switch 59, when actuated sets the counter and requires a series of current alarm signals having a selected difference from the reference level signal. In practice, switch 59 adjusts the threshold in terms of a percentage change. In a practical application, a change of either 9.5 percent or 12.5 percent is set by turning switch 59 on or leaving the switch off.

After initializing of the system, the system will supply power to the unit.

Upon the processor receiving a first wake up signal and a read interrupt, as at point 71. The processor initiates reading of samples. The processor responds to an interrupt after receiving the leading edge of the output signal 47 from the counter. The sample counter has established the pulse train 46 which the processor reads from the front edge of each pulse. In the above described embodiment a two-second sample is recorded as at 72, with processor counter counting high frequency pulses within the frame or cycle of each pulse in pulse train 46 in the sample period, thereby establishing a proportional count signal, as noted at point 72 in FIG. 6. The system as previously described is set up to initially establish four samples to establish a reference base signal. The processor thus determines whether or not the sample taken is in excess of eight, as noted at point 73. If not, it recycles to take the additional samples, as shown by the loop between points 73 and 72. When all four samples have been taken, the processor averages the samples, point 74, determines that the storage buffer is full at point 75. The first average of the count is now placed on the appropriate circulating buffer, as at point 76. The system recycles by stepping to a battery check, point 77, and to power down 71. As previously noted, if a voltage of less than 7.5 volts is detected, a battery alert condition is encountered and a special low battery alarm is activated. The alert may include visual alert at the module and both a visual and audible alarm at the remote station to alert the personnel that the voltage is approaching a level insufficient to operate the system and the battery is to be replaced.

On the next sample interrupt, the next current sample is taken averaged at point 74. The buffer is full and the new sample is placed in an average buffer 78 and compared to the average count stored in the buffer, as at point 79. If the sample is less than the average, there is more weight on the capacitance sensor pad and a normal condition exists. The processes step to determine whether an alarm had been previously set, as at point 80. If not, it immediately steps to put the new sample into the circular buffer at point 76. As previously noted, the loading of the current sample simultaneously therewith removes the first of the four samples existing in the buffer. If the alarm is on, the processor steps to determine if the automatic reset function has been activated, as at 81. If not, the processor steps to place the sample into the buffer at point 76 and recycles. If reset function has been activated, the processor resets the alarm and unfreezes and releases a freeze state of the buffer as at 82, and places the new sample in the buffer 76.

After placing of the sample in the buffer 76, the system recycles through the loop, first checking the battery for undervoltage, as at point 77.

If the next current sample signal is more than the average, this is an indication that less weight appears at the support and consequently may create an abnormal condition. The processor step to the threshold limit check, at point 83. The differential is checked to see if it is more than the threshold limit as set by the switch. If above the level, the processor then steps to freeze the buffer at point 84 steps to increase the alert count, at 85 indicating that at least one alarm condition has been generated. The processor checks to determine whether the count is equal to or greater than the alert limit as at 86, and with switch 58 activated, the limit has been reached. To set the nurse's remote station alarm, as at 87, upon detecting an alarm state, the processor steps to set the nurse's remote station alarm, as at 87, then steps to determine if the local alarm has been muted by operation of switch 57, as at 88. If yes, the processor recycles to the battery check at 77 and again samples the sensor output. If not muted, the local alarm at the module is also set, as at 89 the battery undervoltage checked at 77 and the sample recycled.

If the weight is less than the threshold switch 60 has been activated to insert the automatic reset function, the current signal is also processed through the automatic reset program line 90. If the alarm is not on, the processor check at point 91 so indicates there is no need for reset, and the processor steps to put the sample into the buffer 76. If the alarm is on, the processor step to check to see if the automatic reset function has been activated, at point 92. If not, the processor again steps to put the sample in the buffer 76. If the reset switch 60 was activated, the process resets the alarm off, resets the alert count at 84 to the start count and releases the frozen buffer, and then places the sample in the buffer. If the alert counter is set to require a series of alarm signals, at step 86, the check on a first alarm will be no and the system recycles to a new sample.

If the differential in sequential samples is more than the threshold limit as set by the switch 59, the processor activates the freeze buffer, sequential steps the alert count 85 to its maximum value. The processor on the next sample notes the alert condition and responds as previously discussed with respect to switch 58.

Once the alarm has been set, the apparatus continues to sample. At the position where the new sample is compared with the average in the buffer which has been frozen at the alarm state. If above the average, the processor steps the threshold limit detector. If the sensor has returned to a normal position such that the signal is not above the threshold limit, the processor steps through program line 90 to reset the alarm by determining whether the alarm is on, and whether the auto reset is activated, and then resets all alarms and releases the buffer, thereby resetting the system the same as provided.

Referring to FIG. 7, the signal module is shown having the sensor pad jack 28 and the nurse call jack 53 and an LED lamp 61. The module also includes an on-off switch 62 to enable in the system and a reset button 65 to manually reset the alarm system. Manual reset buttons are also provided at the nurse station 8 as well as at the local module 7. Actuator will reset the alarms, but if the patient is not in fact in a proper condition the next sample will again fire the alarms.

The microprocessor allows the complete inputting and monitoring of the parameter through the software program. The sampling rate, the changes from a previous condition to initiate and set the alert or alarm conditions, the auto reset feature and its limits as required. If necessary, temperature or humidity response variation can be sensed and appropriate compensation established by the program for such sensed conditions.

The capacitance pad is shown with single integral capacitor plates. The capacitor plates may be constructed with a plurality of individual elements in such an arrangement to produce the effective continuously variable capacitance in response to the patient's position and movement with the teaching of this invention. Further, although shown in a preferred construction with a capacitance sensing unit to produce an effective continuously varying signal within the broadest aspect of the invention particularly for the signal processing system, other sensing units which will provide such an effective continuously varying signal may also be used.

The system including the sensor, the signal interface and coupling to a processor has been designed with components selected to operate with a low current drain. The microprocessor is only activated when the interface circuit is operating to establish sampling signals to minimize the current drain.

Because of minimizing the current drain when a battery is used, its operative life is maximized and reduces the requirement of battery replacements.

Reference has been made to patients and residents in describing the invention. Such terminology is used to include any use in which a weight responsive sensor is applied for position and movement sensing based on the novel structure and signal processing system disclosed by the inventors.

Various modes of carrying out the invention are contemplated as being within the scope of the following claims particularly pointing out and distinctly claiming the subject matter which is regarded as the invention.

I claim:

1. A patient support monitor apparatus for sensing selected patient movement within a support structure, comprising a sensing unit adapted to be located within an approved support location of the support structure, said sensing unit establishing an essentially continuously varying position signal in response to the varying weight in said support location, an alert condition unit, a signal processing unit connected to said sensing unit and to said alert condition unit and operable to continuously track said position signal and establishing an alert condition signal in response to a selected change in said position signal in a selected time period, for actuating said alert condition unit, and said signal processing unit including a reset unit responsive to a second selected change in said position signal within a second selected time period to reset said alert condition unit and return said signal processing unit to continuously tracking said position signal.

2. The apparatus of claim 1, having means to establish an alarm response immediately upon sensing said selected change in said position signal in a selected time period.

3. The monitor apparatus of claim 2, wherein a sensing unit is a capacitive pad covering said sensing area inclusive of acceptable patient positions in the support structure.

4. The monitor apparatus of claim 3, wherein said capacitive pad includes compliant capacitive plates which cover said sensing area.

5. The monitor apparatus of claim 3, wherein said pad is constructed to substantially minimize slippage within the support structure.

6. The monitor apparatus of claim 1, including an automatic alert reset responsive to a change in said position signal after actuating said alert condition unit to reset said alert condition unit.

7. The monitor apparatus of claim 1, wherein said signal processing unit only responds to a selected series of said alert condition signals for actuating said alert condition unit to an alert state for controlling the acceptable movement level of the patient.

8. A patient support monitor apparatus for sensing selected patient positions within a support structure, comprising a sensing unit adapted to be located within an approved support location of the support structure, said sensing unit establishing an essentially continuously varying position signal in response to the varying weight in said support location, an alert condition unit, a signal processing unit connected to said sensing unit and operable to continuously track said position signal and establishing a series of successive position-related signals, each being proportioned to said position signal in a selected constant time period, and a comparator unit for continuously comparing the change in said successive position-related signals with a plurality of the preceding position-related signals and establishing an output related to said comparison, a circuit connecting said comparator unit to said alert condition unit for establishing an alert condition output in response to a selected output of said comparator unit.

9. The monitor apparatus of claim 8, wherein a selected change of said position signal within a selected fixed time period which corresponds to a period for which the patient may be away from the sensing unit establishes a "return signal", and said constant time period is substantially greater than said fixed period whereby said return signal alerts the patient to return within said constant time period and prior to creation of an alert condition signal.

10. A patient support monitor comprising a support structural a capacitive sensing pad adapted to be placed under the patient within the support structure, said sensing pad defining a capacitor with spaced capacitive plates and the spacing of plates varying with the position and weight of the patient, a signal processing circuit including a high frequency source coupled to and having an input connected to such capacitive sensing pad and establishing a continuous pulse train signal proportional to the capacitance of said sensing pad, a monitor circuit monitoring the modification of the signal pulse train with variation in said capacitance and thereby defining a parameter signal related directly to the position and movement of the patient, processing said parameter signal for establishing a moving average varying over a short time period on the order of less than five seconds and thereby establishing a reference level signal, a monitor circuit for comparing successive parameter signals with said reference level signal and modifying said reference level signal by each parameter signal within a selected range relative to said reference level signal and thereby providing a continuous tracking of such parameter signal and said weight of the patient, a control output connected to said monitor circuit for continuously comparing said parameter signal with said moving average and establishing alert conditions in response to selected changes in the successive comparisons of the parameter signals and said moving average, said alert condition varying with extraneous selected parameters known to affect the sensed parameters.

11. A capacitive patient sensor device for sensing the position and changes in position of a patient in a support structure, comprising a resilient nonconductive pad of a width to cover an area of the support structure to detect movement within the structure and movement onto and from the structure, compliant conductive plates located on each of the opposite faces of said pad and defining an electrical capacitor and a sensing area, said pad having a selective thickness within said sensing area to establish a selected level of the capacitance of said capacitor in response to a selected minimum body weight in said support structure and a varying output with the change in the position of the patient body on said pad whereby the movement of the patient on said pad as well as the partial and total removal of the patient from said pad is continuously monitored, an outer protective cover enclosing said pad and plates, an electrical cable having wires secured on each of said plates for connecting said plates in a signal processing circuit sensing the body movement over and from said support structures.

12. The capacitive patient sensor device of claim 11, wherein said plates each includes a heavy aluminum foil, and an adhesive secures said foil to said outer protective cover.

13. The capacitive patient sensor device of claim 12, wherein terminals are secured one each to each of said aluminum foils, each of said terminals includes a thin compliant copper element conductively bonded to the corresponding foil, said wires of said electrical cable conductively bonded one each to each of said copper elements.

14. The capacitive patient sensor device of claim 11, wherein said resilient non-conductive pad is a soft foam plastic having a uniform thickness of about one quarter of an inch.

15. The capacitance sensor device of claim 11, wherein said protective cover is constructed and arranged to prevent air movement entrapment by said pad.

16. The capacitive sensor device of claim 11, wherein said protective cover is constructed to minimize slippage on the support structure.

17. The capacitive sensor device of claim 11, wherein said compliant conductive plates cover the sensing area.

* * * * *

UNITED STATES PATENT AND TRADEMARK OFFICE
CERTIFICATE OF CORRECTION

PATENT NO. : 5,410,297

DATED : April 25, 1995

INVENTOR(S) : Peter Joseph et al

It is certified that error appears in the above-identified patent and that said Letters Patent is hereby corrected as shown below:

Column 13, Line 63, CLAIM 11, delete "structural" and substitute therefor ---structure,---.

Signed and Sealed this

Twenty-seventh Day of June, 1995

Attest:

BRUCE LEHMAN

*Attesting Officer*  *Commissioner of Patents and Trademarks*